United States Patent [19]

Riedel et al.

[11] Patent Number: 5,750,752
[45] Date of Patent: May 12, 1998

[54] TRANSITION METAL COMPOUND

[75] Inventors: Michael Riedel, Frankfurt; Frank Küber, Oberursel; Michael Aulbach, Hofheim; Gerhard Erker; Martin Könemann, both of Münster, all of Germany

[73] Assignee: Hoechst Aktiengesellschaft, Frankfurt am Main, Germany

[21] Appl. No.: 668,790

[22] Filed: Jun. 21, 1996

[30]   Foreign Application Priority Data

Jun. 21, 1995  [DE]  Germany ................ 195 22 013.7

[51] Int. Cl.$^6$ ..................... C07F 17/00; B01J 31/00
[52] U.S. Cl. ..................... 556/1; 556/8; 556/11; 556/12; 556/20; 556/21; 556/22; 556/43; 556/53; 556/58; 502/103; 502/117; 534/15; 526/127; 526/160; 526/132; 526/170; 526/943
[58] Field of Search ................ 556/1, 8, 11, 12, 556/20, 21, 22, 43, 53, 58; 534/15; 502/103, 117; 526/170, 943, 127, 132, 160

[56]   References Cited

FOREIGN PATENT DOCUMENTS

| 0520732 | 12/1992 | European Pat. Off. . |
| 0659758 | 6/1995 | European Pat. Off. . |
| 0682037 | 11/1995 | European Pat. Off. . |
| 91/04257 | 4/1991 | WIPO . |
| 95/25112 | 9/1995 | WIPO . |
| 96/00734 | 1/1996 | WIPO . |

*Primary Examiner*—Porfirio Nazario-Gonzalez
*Attorney, Agent, or Firm*—Connolly & Hutz

[57]   ABSTRACT

The present invention relates to a stereorigid transition metal compound having as ligands a cyclopentadienyl group and a substituted or unsubstituted heteroatom which are connected to one another via a monocyclic or polycyclic ring system, with the cyclopentadienyl group being fused onto the monocyclic or polycyclic ring system. The transition metal compound of the invention is suitable as a catalyst component for olefin polymerization.

10 Claims, No Drawings

TRANSITION METAL COMPOUND

The present invention relates to a stereorigid transition metal compound and a process for preparing polyolefins in the presence of this stereorigid transition metal compound.

The preparation of polyolefins using soluble metallocene compounds in combination with aluminoxanes or other cocatalysts which, owing to their Lewis acidity, can convert the neutral metallocene into a cation and stabilize it, is known from the literature (EP 129 368, EP 351 392).

Transition metal compounds in which a π-ligand has been replaced by a heteroatom (eg. N, O, S or P) are known (cf. EP 416 815). The preparation of the compounds described therein proves to be difficult and proceeds in only moderate yields.

Use of soluble metallocene compounds based on bis(cyclopentadienyl)dialkylzirconium or bis(cyclopentadienyl)zirconium dihalide in combination with oligomeric aluminoxanes gives atactic polymers which, owing to their unbalanced and unsatisfactory product properties, are of little industrial importance. In addition, certain olefin copolymers are not obtainable.

Derivatives of zirconocene dichloride, in which the two substituted cyclopentadienyl groups are connected to one another via a methylene, ethylene or dimethylsilylene bridge can, owing to their conformational rigidity, be used as catalysts for the isospecific polymerization of olefins (Chem. Lett. 1989, pp. 1853–1856 or EP-A 0 316 155). Transition metal compounds having (substituted) indenyl radicals as ligands are of particular importance for preparing highly isotactic polymers having a high crystallinity and a high melting point (EP 485 823, EP 530 647).

Of great interest are polymers having a property profile between these two extremes and also certain olefin copolymers.

It is an object of the invention to provide a transition metal compound which avoids the disadvantages of the prior art.

The present invention accordingly provides a transition metal compound having as ligands a cyclopentadienyl group and a substituted or unsubstituted heteroatom which are connected to one another via a monocyclic or polycyclic ring system, with the cyclopentadienyl group being fused onto the monocyclic or polycyclic ring system.

The monocyclic or polycyclic ring system is preferably aliphatic and preferably has 5–15 ring atoms. It can also contain heteroatoms such as silicon, germanium or boron. The monocyclic or polycyclic ring system can also bear substituents such as $C_1$–$C_{40}$-groups.

In determining the number of ring atoms of the monocyclic or polycyclic ring system, those carbon atoms of the cyclopentadienyl group fused onto the ring system which, owing to the fusion, are part of the ring system are counted. Substituents on the monocyclic or polycyclic ring system are not counted here.

For the purposes of the present invention, the term heteroatom means an element of groups IIIa, IVa, Va and VIa of the Periodic Table of the Elements, with the exception of carbon. Preference is given to elements of group Va of the Periodic Table of the Elements, for example nitrogen or phosphorus, and elements of group VIa of the Periodic Table of the Elements, for example oxygen and sulfur. The heteroatoms can bear one or more substituents, such as hydrogen atoms or $C_1$–$C_{20}$-hydrocarbon radicals (e.g. $C_1$–$C_{10}$-alkyl or $C_6$–$C_{14}$-aryl).

The heteroatom is a substituent on the monocyclic or polycyclic ring system (i.e. the heteroatom is bound to the ring system via a covalent bond), while the cyclopentadienyl group is fused onto the monocyclic or polycyclic ring system.

The cyclopentadienyl group is singly (e.g. via the 1,2 or 1,3 positions of the cyclopentadienyl ring) or multiply (e.g. via the 1,2,3 or 1,2,3,4 positions of the cyclopentadienyl ring), preferably singly, fused onto the monocyclic or polycyclic ring system and can bear substituents such as $C_1$–$C_{40}$-groups (e.g. $C_1$–$C_{10}$-alkyl or $C_6$–$C_{20}$-aryl), which can be connected to one another to form rings.

The central unit $M^1Y_k$ of the transition metal compound of the invention preferably comprises a transition metal atom $M^1$, in particular of group IIIb, IVb, Vb or VIb of the Periodic Table of the Elements, which bears k substituents Y which are identical or different and are preferably each a $C_1$–$C_{40}$-group, a halogen atom, an OH group or a hydrogen atom. The number of the substituents Y corresponds to the valency of the transition metal atom $M^1$ minus two.

The present invention preferably provides a transition metal compound of the formula I,

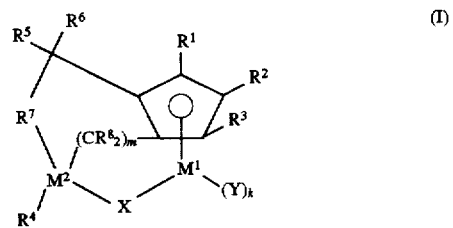

where $M^1$ is a metal of group IIIb, IVb, Vb or VIb of the Periodic Table of the Elements, $M^2$ is carbon, silicon, germanium or boron, X is an unsubstituted or substituted heteroatom such as —O—, —S—, $NR^9$—, $PR^9$—, —$OR^9$, $SR^9$, $NR^9_2$ or $PR^9_2$, where $R^9$ are identical or different and are each a hydrogen atom or a $C_1$–$C_{20}$-hydrocarbon group such as a $C_1$–$C_{10}$-alkyl group or a $C_6$–$C_{10}$-aryl group, or two radicals $R^9$ together with the atoms connecting them can form a ring system, Y are identical or different and are each a hydrogen atom, a $C_1$–$C_{40}$-group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, an OH group, a halogen atom or —$NR^9_3$, where $R^9$ is a halogen atom, a $C_1$–$C_{10}$ alkyl group or a $C_6$–$C_{10}$ aryl group, k is an integer corresponding to the valency of the transition metal atom $M^1$ minus two, $R^1$, $R^2$ and $R^3$ are identical or different and are each a hydrogen atom, a halogen atom, a $C_1$–$C_{20}$-group such as a $C_1$–$C_{10}$-alkyl group, which can be halogenated, a $C_6$–$C_{20}$-aryl group, which can be halogenated, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, an $R^9$—$SiR^9_3$, $NR^9_2$, —$SiOR^9_3$, $SiSR^9_3$ or —$PR^9_2$ radical, where $R^9$ is a halogen atom, a $C_1$–$C_{10}$-alkyl group or a $C_6$–$C_{10}$-aryl group, or two or more adjacent radicals $R^1$, $R^2$ and $R^3$ together with the atoms connecting them form a ring system which preferably contains from 4 to 40, particularly preferably from 6 to 15, carbon atoms, $R^4$ is a hydrogen atom or a $C_1$–$C_{40}$-group such as a $C_1$–$C_{20}$-alkyl group, a $C_1$–$C_{10}$-alkoxy group, a $C_6$–$C_{20}$-aryl group, a $C_6$–$C_{20}$ aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, each of which can bear radicals —$NR^9_3$, $SiR^9_3$-, $SR^9_2$-, —$OSiR^9_3$, where $R^9$ is a halogen atom a $C_1$–$C_{10}$-alkyl group or a $C_6$–$C_{10}$-aryl group.

$R^7$ is

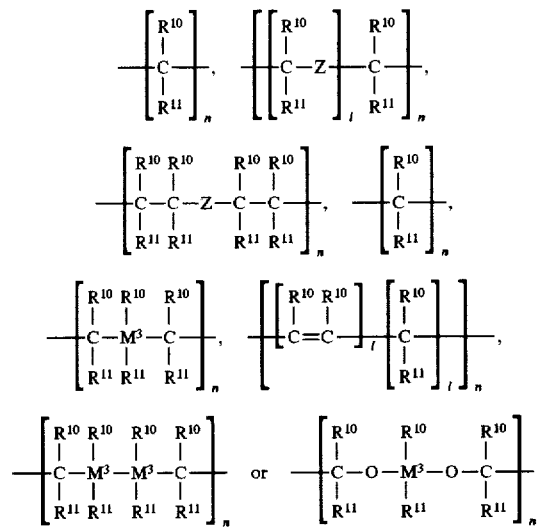

where n is an integer from 1 to 20, I is an integer from 0 to 20, Z is O, =NR$^9$, =CO, =PR$^9$, =P(O)R$^9$, =SO, =SO$^2$ or S, where R$^9$ is a halogen atom, a C$_1$-C$_{10}$-alkyl group or a C$_6$-C$_{10}$-aryl group, R$^{10}$ and R$^{11}$ are identical or different and are each a hydrogen atom, a halogen atom, or a C$_1$-C$_{40}$-group such as a C$_1$-C$_{20}$-alkyl group, a C$_1$-C$_{10}$-fluoroalkyl group, a C$_1$-C$_{10}$-alkoxy group, a C$_6$-C$_{20}$-aryl group, a C$_6$-C$_{20}$-fluoroaryl group, a C$_6$-C$_{20}$-aryloxy group, a C$_2$-C$_{12}$-alkenyl group, a C$_7$-C$_{40}$-arylalkyl group, a C$_7$-C$_{40}$-alkylaryl group or a C$_8$-C$_{40}$-arylalkenyl group, or in each case two radicals R$^{10}$, two radicals R$^{11}$, or one radical R$^{10}$ and one radical R$^{11}$, in each case together with the atoms connecting them, form one or more rings, and M$^3$ is silicon, germanium or tin.

R$^5$ and R$^6$ are identical or different and are each a hydrogen atom or a C$_1$-C$_{40}$-group such as a C$_1$-C$_{20}$-alkyl group, a C$_1$-C$_{10}$-alkoxy group, a C$_6$-C$_{20}$-aryl group, a C$_6$-C$_{20}$-aryloxy group, a C$_2$-C$_{12}$-alkenyl group, a C$_7$-C$_{40}$-arylalkyl group, a C$_7$-C$_{40}$-alkylaryl group or a C$_8$-C$_{40}$-arylalkenyl group, each of which can bear radicals —NR$^9_3$, —SiR$^9_3$-, —SR$^9_2$-, —OSiR$^9_3$, where R$^9$ is a halogen atom, a halogenated or unhalogenated C$_1$-C$_0$-alkyl group or a halogenated or unhalogenated C$_6$-C$_{10}$-aryl group.

R$^8$ are identical or different and are each a hydrogen atom, a halogen atom or a C$_1$-C$_{40}$-group such as a C$_1$-C$_{20}$-alkyl group, a C$_1$-C$_{10}$-alkoxy group, a C$_6$-C$_{20}$-aryl group, a C$_6$-C$_{20}$-aryloxy group, a C$_2$-C$_{12}$-alkenyl group, a C$_7$-C$_{40}$-arylalkyl group, a C$_7$-C$_{40}$-alkylaryl group, or a C$_8$-C$_{40}$-arylalkenyl group or one or more radicals R$^8$ are connected to one or more radicals R$^4$, R$^5$, R$^6$ and R$^7$, and m is an integer from 0 to 24.

For compounds of the formula I, it is preferred that

M$^1$ is an element of group IVb of the Periodic Table of the Elements, for example titanium, zirconium or hafnium, in particular zirconium.

X is NR$^9$, NR$^9_2$, PR$^9_2$ or PR$^9$, in particular NR$^9$ and PR$^9$, where R$^9$ is preferably a C$_1$-C$_4$-alkyl group or a C$_6$-C$_{10}$-aryl group.

Y are identical and are each a C$_1$-C$_4$-alkyl group or a halogen atom, in particular chlorine.

R$^1$, R$^2$ and R$^3$ are identical or different and are each a hydrogen atom, a C$_1$-C$_{10}$-alkyl group or a C$_6$-C$_{20}$-aryl group, or two adjacent radicals R$^1$, R$^2$ and R$^3$ together with the atoms connecting them form an aromatic or aliphatic hydrocarbon ring system which preferably has from 4 to 20 carbon atoms, R$^4$ is a hydrogen atom, a C$_6$-C$_{20}$-aryl group or a C$_1$-C$_{10}$-alkyl group, in particular a C$_1$-C$_4$-alkyl group, R$^7$ is

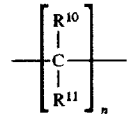

where n is an integer from 1 to 8, in particular from 2 to 4,

R$^{10}$ and R$^{11}$ are identical or different and are each hydrogen or a C$_1$-C$_{10}$-alkyl group, or in each case two radicals R$^{10}$, two radicals R$^{11}$, or one radical R$^{10}$ and one radical R$^{11}$ together with the atoms connecting them form a hydrocarbon ring system, M$^2$ is carbon, R$^5$ and R$^6$ are identical or different and are each a hydrogen atom, a C$_1$-C$_{10}$-alkyl group, in particular a C$_1$-C$_4$-alkyl group, or a C$_6$-C$_{10}$-aryl group, and m =0.

Particular preference is given to compounds of the formula I in which M$^1$ is zirconium, X is NR$^9$, where R$^9$ is a C$_1$-C$_4$-alkyl group such as methyl, ethyl, propyl, isopropyl, butyl or isobutyl, Y are identical and are each a halogen atom, in particular chlorine, R$^1$, R$^2$ and R$^3$ are identical or different and are each hydrogen, a C$_1$-C$_4$-alkyl group such as methyl, ethyl, propyl, isopropyl, butyl or isobutyl or a C$_6$-C$_{14}$-aryl group such as phenyl or naphthyl, or R$^1$ and R$^2$ or R$^2$ and R$^3$ together with the atoms connecting them form an aromatic hydrocarbon ring system, in particular a six-membered ring, which in turn can be substituted, M$^2$ is a carbon atom, R$^4$ is a C$_1$-C$_6$-alkyl group, in particular methyl, or a C$_6$-C$_{20}$-aryl group, in particular phenyl, R$^{11}$ is —CH$_2$— or —CH$_2$-CH$_2$—.

R$^5$ and R$^6$ are identical or different and are each a methyl group, a phenyl group or hydrogen, and m =0.

Examples of transition metal compounds of the invention are:

4-(methylamido)-7,7-dimethyl-4-phenyl-($\eta^5$-4,5,6,7-tetrahydroindenyl)dichlorozirconium 4-(methylamido)-7,7-dimethyl-4-phenyl-($\eta^5$-4,5,6,7-tetrahydroindenyl)dichlorotitanium 4-(methylamido)-4,7,7-trimethyl-($\eta^5$-4,5,6,7-tetrahydroindenyl)dichlorozirconium 4-(methylamido)-4,7,7-trimethyl-($\eta^5$-4,5,6,7-tetrahydroindenyl)dichlorotitanium 4-(methylamido)-7,7-dimethyl-($\eta^5$-4, 5,6,7-tetrahydroindenyl)dichlorozirconium 4-(methylamido)-7,7-dimethyl-($\eta^5$-4,5,6,7-tetrahydroindenyl)dichlorotitanium 4-(methylamido)-4,7,7-triphenyl-($\eta^5$-4,5,6,7-tetrahydroindenyl)dichlorozirconium 4-(methylamido)-4,7,7-triphenyl-($\eta^5$-4,5,6,7-tetrahydroindenyl)dichlorotitanium 4-(methylamido)-4-methyl-7,7-diphenyl-($\eta^5$-4,5,6,7-tetrahydroindenyl)dichlorozirconium 4-(methylamido)-4-methyl-7,7-diphenyl-($\eta^5$-4,5,6,7-tetrahydroindenyl)dichlorotitanium 4-(methylamido)-7,7-diphenyl-($\eta^5$-4,5,6,7-tetrahydroindenyl)dichlorozirconium 4-(methylamido)-7,7-diphenyl-($\eta^5$-4,5,6,7-tetrahydroindenyl)dichlorotitanium 4-(methylamido)-6,6-dimethyl-4-phenyl-($\eta^5$-4,5-tetrahydropentalene)dichlorozirconium 4-(methylamido)-6,6-dimethyl-4-phenyl-($\eta^5$-4, 5-tetrahydropentalene)dichlorotitanium
4-(methylamido)-4,6,6-trimethyl-($\eta^5$-4,5-tetrahydropentalene)dichlorozirconium
4-(methylamido)-4,6,6-trimethyl-($\eta n^5$-4,5-tetrahydropentalene)dichlorotitanium
4-(methylamido)-6,6-dimethyl-($\eta^5$-4,5-tetrahydropentalene)dichlorozirconium
4-(methylamido)-6,6-dimethyl-($\eta^5$-4,5-tetrahydropentalene)dichlorotitanium
4-(methylamido)-4,6,6-triphenyl-($\eta^5$-4,5-tetrahydropentalene)dichlorozirconium
4-(methylamido)-4,6,6-triphenyl-($\eta^5$-4,5-tetrahydropentalene)dichlorotitanium
4-(methylamido)-4-methyl-6,6-diphenyl-($\eta^5$-4,5-tetrahydropentalene)dichlorozirconium
4-(methylamido)-4-methyl-6,6-diphenyl-($\eta^5$-4,5-tetrahydropentalene)dichlorotitanium
4-(methylamido)-6,6-diphenyl-($\eta^5$-4,5-tetrahydropentalene)dichlorozirconium
4-(methylamido)-6,6-diphenyl-($\eta^5$-4,5-tetrahydropentalene)dichlorotitanium
4-(methylamido)-2-isopropyl-6,6-dimethyl-4-phenyl-($\eta^5$-4,5,6,7-tetrahydroindenyl)dichlorozirconium
4-(methylamido)-2-isopropyl-6,6-dimethyl-4-phenyl-($\eta^5$-4,5,6,7-tetrahydroindenyl)dichlorotitanium
4-(methylamido)-2-tert-butyl-4, 6,6-trimethyl-($\eta^5$-4,5-tetrahydropentalene)dichlorozirconium
4-(methylamido)-2-tert-butyl-4,6,6-trimethyl-($\eta^5$-4,5-tetrahydropentalene)dichlorotitanium.

The naming of the abovementioned transition metal compounds of the invention is illustrated by means of the compound 4-(methylamido)-2-isopropyl-4,6,6-trimethyl-($\eta^5$-4,5-tetrahydropentalene)dichlorozirconium. The ring system which connects the cyclopentadienyl radical to the heteroatom has five carbon atoms (C4, C5, C6, C7, C8) and three methyl substituents. The cyclopentadienyl group bears an isopropyl radical in the 2 position and is singly fused onto the ring system, while the heteroatom is covalently bonded to the ring system and has a methyl substituent.

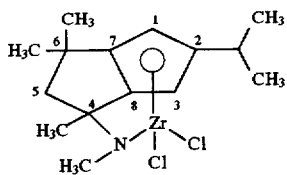

The preparation of the transition metal compound of the invention is illustrated by the following reaction scheme for metallocenes of the formulae VI and XIII. Here, $M^4$ is a metal of main group Ia, IIa or IIIa and R is a $C_1$–$C_{20}$-hydrocarbon radical such as $C_1$–$C_{10}$-alkyl or $C_6$–$C_{14}$-aryl.

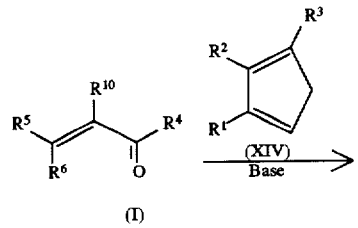

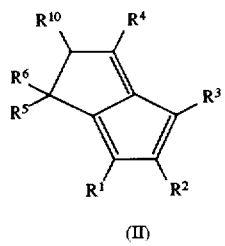

(II)

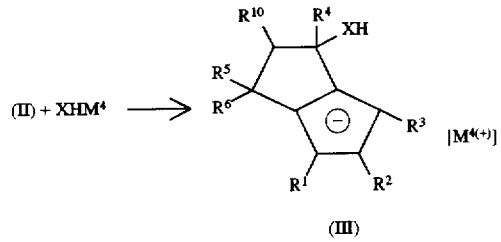

(III)

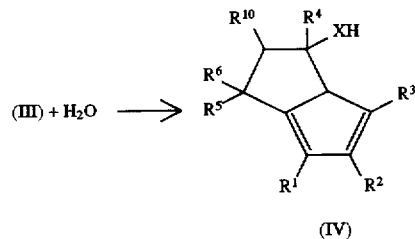

(IV)

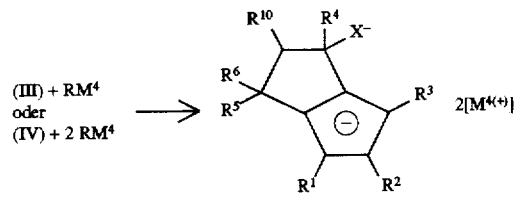

(V)

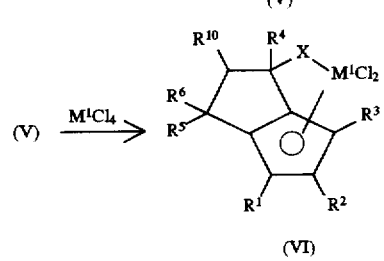

(VI)

The compounds of the formula II can be prepared from α,β-unsaturated ketones (Chem. Ber. 1123, 549 (1990), J. Org. Chem. 54, 4981 (1989)) by literature methods. The compounds of the formula II are converted into the ligand system III by reaction with an organometallic compound (for example lithium methylamide, sodium tert-butylamide) or Grignard amide reagents.

The salts of the formula III can be directly converted into the corresponding dianion compounds of the formula V by deprotonation with, for example, butyllithium. Hydrolysis of the compound III forms the ligand IV which is obtained as a mixture of constitutional isomers and can be purified by chromatography. Double deprotonation of IV with, for example, butyllithium forms the dianion compound of the formula V.

The conversion into the transition metal compounds of the formula VI and the isolation of the desired complexes is known in principle. For this purpose, the dianion of the formula V in an inert solvent is reacted with the corresponding metal halide such as zirconium tetrachloride.

Suitable solvents are aliphatic or aromatic solvents such as hexane or toluene, ether solvents such as tetrahydrofuran or diethyl ether, or halogenated hydrocarbons such as methylene chloride, or halogenated aromatic hydrocarbons such as o-dichlorobenzene.

A further possible way of preparing the transition metal compounds of the invention comprises reacting the ligand precursor VIII with cyclopentadiene to form the cyclization precursor IX, whose cyclization can be induced by the reaction with an organometallic compound (for example dimethyllithiumcopper or higher cuprates). The conversion of X into XI is carried out using an organometallic compound such as lithium methylamide, sodium tert-butylamide or Grignard amide reagents.

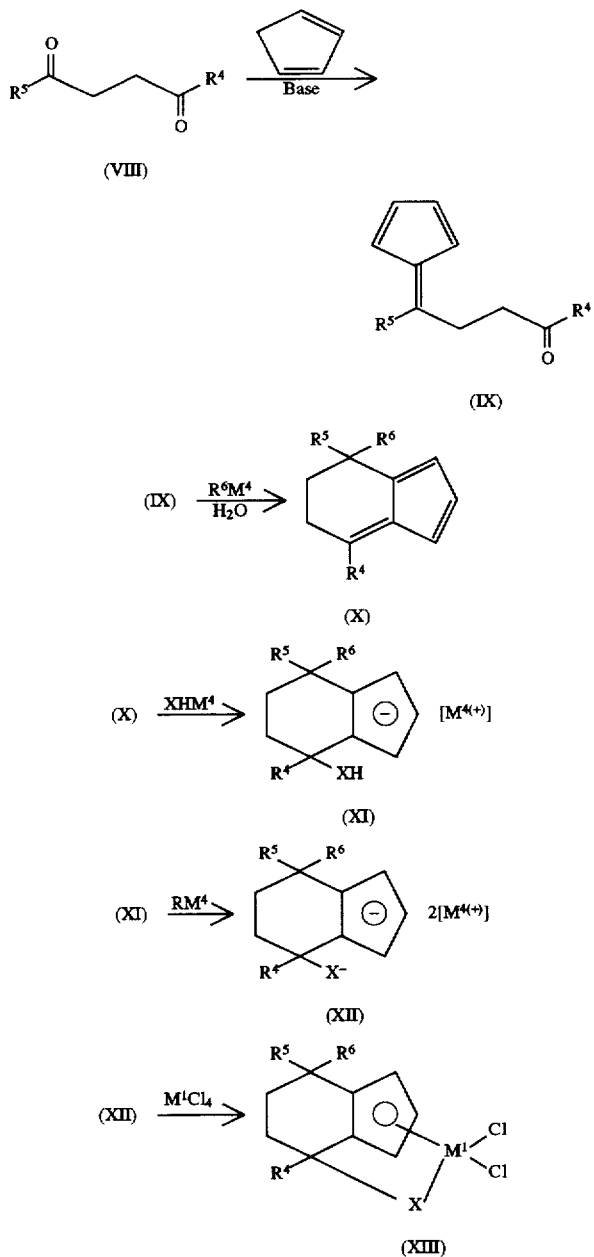

The dianion compounds of the formula XII can be obtained directly by reaction of XI with an organometallic reagent (e.g. butyllithium). The conversion into the transition metal compounds of the formula XII and the isolation of the desired complexes is known in principle. For this purpose, the dianion of the formula V in an inert solvent is reacted with the corresponding metal halide such as zirconium tetrachloride.

Suitable solvents are aliphatic or aromatic solvents such as hexane or toluene, ether solvents such as tetrahydrofuran or diethyl ether or halogenated hydrocarbons such as methylene chloride or halogenated aromatic hydrocarbons such as o-dichlorobenzene.

The transition metal compounds of the invention are highly active catalyst components for olefin polymerization. Depending on the substitution pattern of the ligands, the transition metal compounds can be obtained as a mixture of isomers. The transition metal compounds are preferably used as pure isomers, but can also be used as a mixture of isomers.

The present invention also provides a process for preparing a polyolefin by polymerization of one or more olefins in the presence of a stereorigid transition metal compound having as ligands a cyclopentadienyl group and an unsubstituted or substituted heteroatom which are connected to one another via a monocyclic or polycyclic ring system, with the cyclopentadienyl group being fused onto the monocyclic or polycyclic ring system. For the purposes of the present invention, the term polymerization includes both homopolymerization and copolymerization.

In the process of the invention, preference is given to polymerizing one or more olefins of the formula $R^a$—CH=CH—$R^b$ where $R^a$ and $R^b$ are identical or different and are each a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins having 1–20 carbon atoms, for example ethylene, propene, 1-butene, 1-pentene, 1-hexene, 4-methyl-1pentene or 1-octene, styrene, cyclic or acyclic dienes such as 1,3-butadiene, isoprene, 1,4-hexadiene, norbornadiene, vinylnorbornene, 5-ethylidenenorbornene or cyclic monoolefins such as norbornene or tetracyclododecene. In the process of the invention, preference is given to homopolymerizing ethylene or propylene or copolymerizing ethylene with one or more acyclic 1-olefins having from 3 to 20 carbon atoms, for example propylene and/or one or more dienes having from 4 to 20 carbon atoms, for example 1,3-butadiene.

The polymerization is preferably carried out at a temperature of from –60° to 250° C., particularly preferably from 50 to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. A preferred embodiment is gas-phase polymerization.

The catalyst used in the process of the invention preferably comprises one stereorigid transition metal compound. It is also possible to use mixtures of two or more stereorigid transition metal compounds or mixtures with metallocenes, e.g. for preparing olefins having a broad or multimodal molecular weight distribution.

In principle, a suitable cocatalyst in the process of the invention is any compound which, owing to its Lewis acidity, can convert the neutral transition metal compound into a cation and stabilize it ("labile coordination"). In addition, the cocatalyst or the anion formed therefrom should undergo no further reactions with the cation formed (EP 427 697). As cocatalyst, preference is given to using an aluminum compound and/or a boron compound.

The boron compound preferably has the formula $R^{12}_xNH_{4-x}BR^{13}_4$, $R^{12}_xPH_{4-x}BR^{13}_{44}$, $R^{12}_3CBR^{13}_4$ or $BR^{13}{}_3$, where x is a number from 1 to 4, preferably 3, the radicals $R^{12}$ are identical or different, preferably identical, and are $C_1$–$C_{10}$-alkyl or $C_6$–$C_{18}$-aryl or two radicals $R^{12}$ together with the atoms connecting them form a ring, and the radicals $R^{13}$ are identical or different, preferably identical, and are $C_6$–$C_{18}$-aryl which can be substituted by alkyl, haloalkyl or fluorine. In particular, $R^{12}$ is ethyl, propyl, butyl or phenyl and $R^{13}$ is phenyl, pentafluorophenyl, 3,5-bis (trifluoromethyl)phenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula IIa for the linear type and/or the formula IIb for the cyclic type.

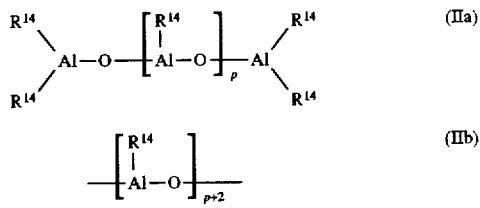

where, in the formulae IIa and IIb, the radicals $R^{14}$ are identical or different and are each hydrogen or a $C_1$–$C_{20}$-hydrocarbon group such as a $C_1$–$C_{18}$-alkyl group, a $C_6$–$C_{18}$-aryl group or benzyl, and p is an integer from 2 to 50, preferably from 10 to 35.

The radicals $R^{14}$ are preferably identical and are hydrogen, methyl, isobutyl, phenyl or benzyl, particularly preferably methyl.

If the radicals $R^{14}$ are different, they are preferably methyl and hydrogen or alternatively methyl and isobutyl, with hydrogen or isobutyl preferably being present in a numerical proportion of from 0.01 to 40 % (of the radicals $R^{14}$).

The methods of preparing the aluminoxane are known. The exact spatial structure of the aluminoxanes is not known (J. Am. Chem. Soc. (1993) 115, 4971). For example, it is conceivable that chains and rings connect to form larger two-dimensional or three-dimensional structures.

Regardless of the method of preparation, all aluminoxane solutions have in common a varying content of unreacted aluminum starting compound which is present in free form or as adduct.

It is possible to preactivate the transition metal compound with a cocatalyst, in particular an aluminoxane prior to use in the polymerization reaction. This significantly increases the polymerization activity. The preactivation of the transition metal compound is preferably carried out in solution. In the preactivation, the transition metal compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1 % by weight to the saturation limit, preferably from 5 to 30 % by weight, in each case based on the total amount of solution. The transition metal compound can be used in the same concentration, but it is preferably used in an amount of from $10^{-4}$ to 1 mol per mol of aluminoxane. The preactivation time is from 5 minutes to 60 hours, preferably from 5 to 60 minutes. The preactivation is carried out at a temperature of from $-78°$ to $150°$ C., preferably from $0°$ to $80°$ C.

The transition metal compound is preferably employed in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is preferably used in a concentration of from $10^{-6}$ to $10^{-1}$ mol, preferably from $10^{-5}$ to $10^{-2}$ mol, per $dm^3$ of solvent or per $dm^3$ of reactor volume. The other cocatalysts mentioned are used in approximately equimolar amounts to the transition metal compound.

However, higher concentrations are also possible in principle.

The aluminoxane can be prepared in various ways by known methods. One of the methods is, for example, reacting an aluminum-hydrocarbon compound and/or a hydridoaluminum-hydrocarbon compound with water (gaseous, solid, liquid or bound, for example as water of crystallization) in an inert solvent (for example toluene). To prepare an aluminoxane having different radicals $R^{14}$, for example, two different trialkylaluminums corresponding to the desired composition are reacted with water.

To remove catalyst poisons present in the olefin, a purification using an aluminum compound, preferably an aluminum alkyl such as trimethylaluminum or triethylaluminum, is advantageous. This purification can be carried out either in the polymerization system itself or the olefin is, prior to addition to the polymerization system, brought into contact with the aluminum compound and subsequently separated off again.

As molecular weight regulator and/or for increasing the catalyst activity, hydrogen can be added in the process of the invention. This enables low molecular weight polyolefins such as waxes to be obtained.

In the process of the invention, the transition metal compound is preferably reacted with the cocatalyst outside the polymerization reactor in a separate step using a suitable solvent. Application to a support can be carried out during this procedure.

In the process of the invention, a prepolymerization can be carried out with the aid of the transition metal compound. The prepolymerization is preferably carried out using the (or one of the) olefin(s) used in the polymerization.

The catalyst used in the process of the invention can be supported. Application to a support enables, for example, the particle morphology of the polyolefin prepared to be controlled. The transition metal compound can be reacted first with the support and subsequently with the cocatalyst. The cocatalyst can also be supported first and subsequently reacted with the transition metal compound. It is also possible to support the reaction product of transition metal compound and cocatalyst. Suitable support materials are, for example, silica gels, aluminum oxides, solid aluminoxane or other inorganic support materials such as magnesium chloride. Another suitable support material is a polyolefin powder in finely divided form. The preparation of the supported cocatalyst can be carried out, for example, as described in EP 567 952.

Preference is given to applying the cocatalyst, e.g. aluminoxane, to a support such as silica gel, aluminum oxide, solid aluminoxane, another inorganic support material or a polyolefin powder in finely divided form and then reacting it with the metallocene.

As inorganic supports, it is possible to use oxides which have been produced flame-pyrolytically by combustion of element halides in a hydrogen/oxygen flame, or which can be prepared as silica gels in particular particle size distributions and particle shapes.

Possible ways of preparing a supported cocatalyst are described in EP 578 838.

For this purpose, the transition metal compound of the invention can be applied to the supported cocatalyst by stirring the dissolved transition metal compound with the supported cocatalyst. The solvent is removed and replaced by a hydrocarbon in which both cocatalyst and the transition metal compounds are insoluble.

The reaction to form the supported catalyst system is carried out at a temperature of from −20° to +120° C., preferably from 0° to 100° C., particularly preferably from 15° to 40° C. The transition metal compound is preferably reacted with the supported cocatalyst by combining the cocatalyst as a suspension containing from 1 to 40 % by weight, preferably from 5 to 20 % by weight, of cocatalyst in an aliphatic, inert suspension medium such as n-decane, hexane, heptane, or diesel oil with a solution of the transition metal compound in an inert solvent such as toluene, hexane, heptane or dichloromethane, or with the finely ground solid of the transition metal compound. The other way round, a solution of the transition metal compound can also be reacted with the solid cocatalyst.

The reaction is carried out by intensive mixing, for example by stirring, at a molar Al/M$^1$ ratio of from 100/1 to 10000/1, preferably from 100/1 to 3000/1, for a reaction time of from 5 to 120 minutes, preferably from 10 to 60 minutes, particularly preferably 10 to 30 minutes, under inert conditions.

During the course of the reaction for preparing the supported catalyst system, particularly when using a transition metal compound of the invention having absorption maxima in the visible range, changes occur in the color of the reaction mixture, and the progress of the reaction can be followed by means of these changes.

After the reaction time has elapsed, the supernatant solution is separated off, for example by filtration or decantation. The remaining solid is washed from 1 to 5 times with an inert suspension medium such as toluene, n-decane, hexane, diesel oil, or dichloromethane to remove soluble constituents in the catalyst formed, in particular to remove unreacted and therefore soluble transition metal compounds.

The supported catalyst system thus prepared can, as a vacuum-dried powder or while still wet with solvent, be resuspended and metered as a suspension in one of the abovementioned inert suspension media into the polymerization system.

If polymerization is carried out as a suspension or solution polymerization, an inert solvent customary for the Ziegler low-pressure process is used. For example, the polymerization is carried out in an aliphatic or cycloaliphatic hydrocarbon, examples being propane, butane, hexane, heptane, isooctane, cyclohexane and methylcyclohexane. It is also possible to use a petroleum or hydrogenated diesel oil fraction. Toluene can also be used. Preference is given to carrying out the polymerization in the liquid monomer.

Before addition of the catalyst, in particular the supported catalyst system (comprising the transition metal compound of the invention and a supported cocatalyst), it is possible to additionally add another aluminum alkyl compound such as trimethylaluminum, triethylaluminum, triisobutylaluminum, trioctylaluminum or isoprenylaluminum to the reactor in order to make the polymerization system inert (for example to remove catalyst poisons present in the olefin). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This enables a small molar Al/M$^1$ ratio to be selected in the synthesis of a supported catalyst system.

If inert solvents are used, the monomers are preferably metered in in gaseous or liquid form.

The special stereorigid transition metal compounds described in the present invention are suitable for preparing polyolefins. These are particularly suitable for producing shaped bodies such as films, plates or large hollow bodies (e.g. tubes) and can also be used as plasticizer and lubricant formulations, melt adhesive applications, coatings, seals, insulation, filling compounds or sound insulation materials.

We claim:

1. A stereorigid transition metal compound having as ligands a cyclopentadienyl group and a substituted or unsubstituted heteroatom which are connected to one another via a monocyclic or polycyclic ring system, with the cyclopentadienyl group being fused onto the monocyclic or polycyclic ring system.

2. A stereorigid transition metal compound as claimed in claim 1, wherein the monocyclic or polycyclic ring system is aliphatic.

3. A stereorigid transition metal compound as claimed in claim 1, wherein the heteroatom bears one or more substituents which are identical or different and are each a hydrogen atom or a $C_1$–$C_{20}$-hydrocarbon radical.

4. A stereorigid transition metal compound as claimed in claim 1 having the formula I

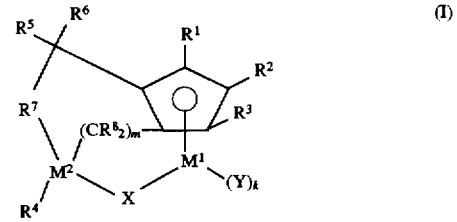

where M$^1$ is a metal of group IIIb, IVb, Vb or VIb of the Periodic Table of the Elements, M$^2$ is carbon, silicon, germanium or boron, X is an unsubstituted or substituted heteroatom, Y are identical or different and are each a hydrogen atom, a $C_1$–$C_{40}$-group, an OH group, a halogen atom or —NR$^9{}_2$, where R$^9$ is a halogen atom, a $C_1$–$C_{10}$ alkyl group or a $C_6$–$C_{10}$ aryl group, k is an integer corresponding to the valency of the transition metal atom M$^1$ minus two, R$^1$, R$^2$ and R$^3$ are identical or different and are each a hydrogen atom, a halogen atom, a $C_1$–$C_{20}$-group, an R$^9$—SiR$^9{}_3$, NR$^9{}_2$, —SiOR$^9{}_3$, SiSR$^9{}_3$ or —PR$^9{}_2$ radical, where R$^9$ is a halogen atom, a $C_1$–$C_{10}$-alkyl group or a $C_6$–$C_{10}$-aryl group, or two or more adjacent radicals R$^1$, R$^2$ and R$^3$ together with the atoms connecting them form a ring system, R$^4$ is a hydrogen atom or a $C_1$–$C_{40}$-group, R$^7$ is

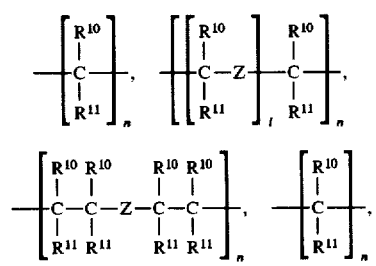

-continued

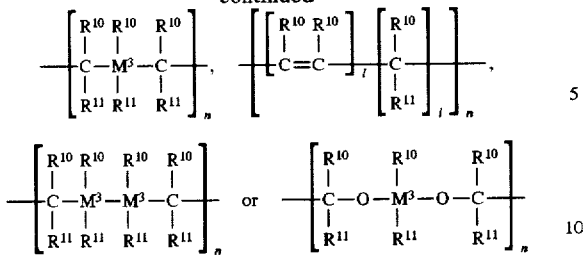

where n is an integer from 1 to 20, I is an integer from 0 to 20, Z is O, =NR$^9$, =CO, =PR$^9$, =P(O)R$^9$, =SO, =SO$^2$ or S, where R$^9$ is a halogen atom, a $C_1$–$C_{10}$-alkyl group or a $C_6$–$C_{10}$-aryl group, R$^{10}$ and R$^{11}$ are identical or different and are each a hydrogen atom, a halogen atom or a $C_1$–$C_{40}$-group or in each case two radicals R$^{10}$, two radicals R$^{11}$ or one radical R$^{10}$ and one radical R$^{11}$,in each case together with the atoms connecting them, form one or more rings, and M$^3$ is silicon, germanium or tin, R$^5$ and R$^6$ are identical or different and are each a hydrogen atom or a $C_1$–$C_{40}$-group, R$^8$ are identical or different and are each a hydrogen atom, a halogen atom or a $C_1$–$C_{40}$-group, or one or more radicals R$^8$ are connected to one or more radicals R$^4$, R$^5$, R$^6$ and R$^7$, and m is an integer from 0 to 24.

5. A stereorigid transition metal compound as claimed in claim 4, wherein

M$^1$ is titanium, zirconium or hafnium,

X is NR$^9$, NR$^9{}_2$, PR$^9{}_2$ or PR$^9$, where R$^9$ is a $C_1$–$C_4$-alkyl group or a $C_6$–$C_{10}$-aryl group, Y are identical and are each a $C_1$–$C_4$-alkyl group or a halogen atom, R$^1$, R$^2$ and R$^3$ are identical or different and are each a hydrogen atom, a $C_1$–$C_{10}$-alkyl group or a $C_6$–$C_{20}$-aryl group, or two adjacent radicals R$^1$, R$^2$ and R$^3$ together with the atoms connecting them form an aromatic or aliphatic hydrocarbon ring system, R$^4$ is a hydrogen atom, a $C_6$–$C_{20}$-aryl group or a $C_1$–$C_{10}$-alkyl group, R$^7$ is

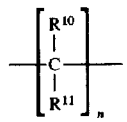

where n is an integer from 1 to 8, R$^{10}$ and R$^{11}$ are identical or different and are each hydrogen or a $C_1$–$C_{10}$-alkyl group, or in each case two radicals R$^{10}$, two radicals R$^{11}$, or one radical R$^{10}$ and one radical R$^{11}$ together with the atoms connecting them form a hydrocarbon ring system, M$^2$ is carbon, R$^5$ and R$^6$ are identical or different and are each a hydrogen atom, a $C_1$–$C_{10}$-alkyl group or a $C_6$–$C_{10}$-aryl group and m=0.

6. A stereorigid transition metal compound as claimed in claim 4, wherein

M$^1$ is zirconium, X is NR$^9$, where R$^9$ is a $C_1$–$C_4$-alkyl group such as methyl, ethyl, propyl, isopropyl, butyl or isobutyl, Y are identical and are each a halogen atom, R$^1$, R$^2$ and R$^3$ are identical or different and are each hydrogen, a $C_1$–$C_4$-alkyl group or a $C_6$–$C_{14}$-aryl group, or R$^1$ and R$^2$ or R$^2$ and R$^3$ together with the atoms connecting them form an aromatic hydrocarbon ring system, M$^2$ is a carbon atom, R$^4$ is a $C_1$–$C_6$-alkyl group or a $C_6$–$C_{20}$-aryl group, R$^{11}$ is —CH$_2$— or —CH$_2$—CH$_2$—, R$^5$ and R$^6$ are identical or different and are each a methyl group, a phenyl group or hydrogen, and m =0.

7. A catalyst comprising at least one stereorigid transition metal compound as claimed in claim 1 and at least one cocatalyst.

8. A catalyst as claimed in claim 7, wherein the cocatalyst is an aluminum compound and/or a boron compound.

9. A process for preparing a polyolefin by polymerization of one or more olefins in the presence of a catalyst as claimed in claim 7.

10. The process as claimed in claim 9, wherein the olefins polymerized are one or more olefins of the formula R$^a$—CH=CH—R$^b$, where R$^a$ and R$^b$ are identical or different and are each a hydrogen atom or a hydrocarbon radical having from 1 to 20 carbon atoms, or R$^a$ and R$^b$ together with the atoms connecting them form one or more rings.

* * * * *